(12) United States Patent
Vuorenmaa et al.

(10) Patent No.: US 9,789,143 B2
(45) Date of Patent: *Oct. 17, 2017

(54) USE OF TALL OIL FATTY ACID

(71) Applicant: Hankkija Oy, Hyvinkää (FI)

(72) Inventors: Juhani Vuorenmaa, Hyvinkää (FI); Hannele Kettunen, Tervakoski (FI)

(73) Assignee: Hankkija Oy, Hyvinkaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/891,089

(22) PCT Filed: May 9, 2014

(86) PCT No.: PCT/FI2014/050348
§ 371 (c)(1),
(2) Date: Nov. 13, 2015

(87) PCT Pub. No.: WO2014/184432
PCT Pub. Date: Nov. 20, 2014

(65) Prior Publication Data
US 2016/0089407 A1 Mar. 31, 2016

(30) Foreign Application Priority Data

May 14, 2013 (FI) .................................. 20135506

(51) Int. Cl.
| | | |
|---|---|---|
| *A01N 37/00* | (2006.01) | |
| *A61K 36/15* | (2006.01) | |
| *A61K 36/13* | (2006.01) | |
| *A61K 31/19* | (2006.01) | |
| *A61K 31/20* | (2006.01) | |
| *A23K 20/158* | (2016.01) | |
| *A23K 50/10* | (2016.01) | |
| *A23L 33/115* | (2016.01) | |

(52) U.S. Cl.
CPC ............ *A61K 36/15* (2013.01); *A23K 20/158* (2016.05); *A23K 50/10* (2016.05); *A23L 33/115* (2016.08); *A61K 31/19* (2013.01); *A61K 31/20* (2013.01); *A61K 36/13* (2013.01); *A23V 2002/00* (2013.01); *Y02P 60/56* (2015.11)

(58) Field of Classification Search
CPC ....................................................... A61K 36/15
USPC ........................................................ 514/558
See application file for complete search history.

(56) References Cited

U.S. PATENT DOCUMENTS

| | | | |
|---|---|---|---|
| 2,240,365 A | 4/1941 | Dreger | |
| 2,308,431 A | 1/1943 | Brandt | |
| 2,423,236 A | 7/1947 | Harwood et al. | |
| 2,481,356 A | 9/1949 | Segessemann et al. | |
| 2,530,810 A | 11/1950 | Christenson et al. | |
| 2,611,706 A | 9/1952 | Bernhart et al. | |
| 2,736,663 A | 2/1956 | Weber | |
| 2,854,420 A | 9/1958 | Clark et al. | |
| 2,866,739 A | 12/1958 | Ciesielski et al. | |
| 2,894,939 A | 7/1959 | Hampton | |
| 2,941,941 A | 6/1960 | Groll | |
| 2,987,183 A | 6/1961 | Bishop | |
| 3,001,962 A | 9/1961 | Carlston | |
| 3,009,820 A | 11/1962 | Gould | |
| 3,066,160 A | 11/1962 | Hampton | |
| 3,141,897 A | 7/1964 | Crecelius et al. | |
| 3,175,916 A | 3/1965 | Costigliola et al. | |
| 3,194,728 A | 7/1965 | Stump, Jr. | |
| 3,257,438 A | 6/1966 | Wicke et al. | |
| 3,311,561 A | 3/1967 | Amderson et al. | |
| 3,458,625 A | 7/1969 | Ensor et al. | |
| 3,691,211 A | 9/1972 | Julian | |
| 3,830,789 A | 8/1974 | Garrett et al. | |
| 3,887,537 A | 6/1975 | Harada et al. | |
| 3,926,936 A | 12/1975 | Lehtinen | |
| 4,000,271 A | 12/1976 | Kremer et al. | |
| 4,076,700 A | 2/1978 | Harada et al. | |
| 4,118,407 A | 10/1978 | Red et al. | |
| 4,313,940 A | 2/1982 | Pasarela | |
| 4,437,894 A | 3/1984 | Emerson | |
| 4,443,437 A | 4/1984 | Prokosch et al. | |
| 4,810,299 A | 3/1989 | Schilling et al. | |
| 4,810,534 A | 3/1989 | Seaborne et al. | |
| 5,428,072 A | 6/1995 | Cook et al. | |
| 5,460,648 A | 10/1995 | Walloch et al. | |
| 6,020,377 A | 2/2000 | O'Quinn et al. | |
| 6,229,031 B1 | 5/2001 | Strohmaier et al. | |
| 6,608,222 B2 | 8/2003 | Bonsignore et al. | |
| 8,741,171 B2 | 6/2014 | Swift et al. | |
| 9,358,218 B2 | 6/2016 | Vuorenmaa et al. | |
| 9,422,507 B2 | 8/2016 | Hamunen | |

(Continued)

FOREIGN PATENT DOCUMENTS

| | | |
|---|---|---|
| CA | 2 107 647 A1 | 4/1994 |
| CN | 101461443 A | 6/2009 |

(Continued)

OTHER PUBLICATIONS

McGuire, Journal of Chromatographic Science, vol. 36, Feb. 1998 104-108.*
Bannink, Animal Feed Science and Technology 166-167 (2011) 603-618.*
Patra, Asian Journal of Animal and Veterinary Advances 6 (5): 416-428, 2011.*
Machmuler et al. Animal Feed Science Technology 71, 1998. 117-130.*
Zhou et al. Archaea, vol. 2013, Article ID 106916, 1-9.*
Polan, Journal of Bacteriology, vol. 88, No. 4, 1056-1064, 1964.*

(Continued)

*Primary Examiner* — Nizal Chandrakumar
(74) *Attorney, Agent, or Firm* — Merchant & Gould P.C.

(57) ABSTRACT

The present invention relates to use of a tall oil fatty acid in enhancing rumen fermentation and/or lowering rumen methane production. The invention further relates to use of a feed supplement and a feed composition comprising tall oil fatty acid.

9 Claims, 1 Drawing Sheet

(56) References Cited

U.S. PATENT DOCUMENTS

Figure 1:
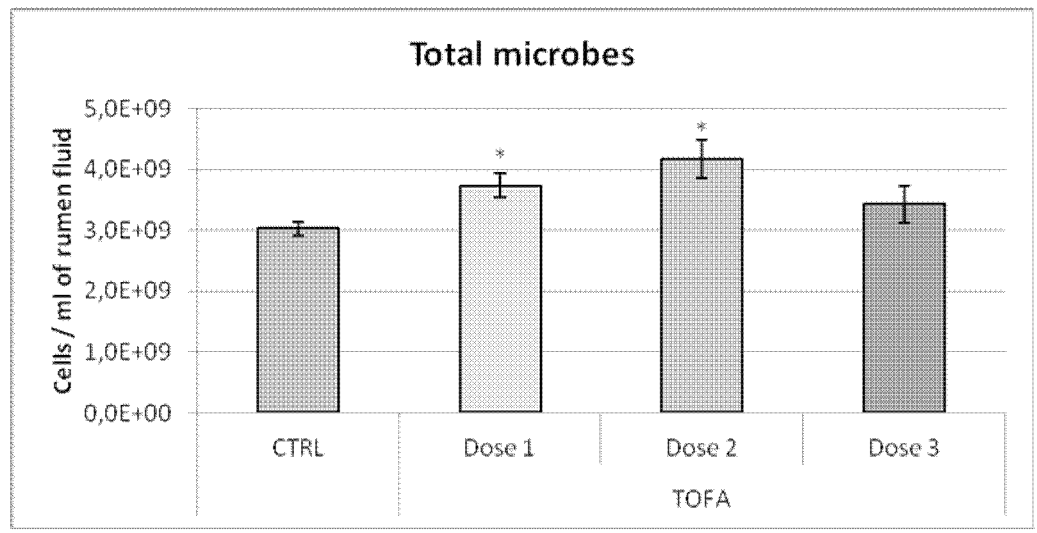

| | | |
|---|---|---|
| 2002/0147356 A1 | 10/2002 | Bonsignore et al. |
| 2002/0183298 A1 | 12/2002 | Schersl et al. |
| 2003/0144536 A1 | 7/2003 | Sonnier et al. |
| 2005/0107582 A1 | 5/2005 | Wong et al. |
| 2005/0203279 A1 | 9/2005 | Rojas et al. |
| 2006/0021276 A1 | 2/2006 | Sonnier |
| 2006/0286185 A1 | 12/2006 | Prokosch |
| 2008/0262251 A1 | 10/2008 | Sato et al. |
| 2009/0012164 A1 | 1/2009 | Kelderman |
| 2009/0220638 A1 | 9/2009 | Perez |
| 2009/0277972 A1 | 11/2009 | Kennon et al. |
| 2009/0285931 A1 | 11/2009 | Shelby et al. |
| 2009/0297687 A1 | 12/2009 | Ramirez et al. |
| 2011/0081442 A1 | 4/2011 | Weill et al. |
| 2011/0200570 A1 | 8/2011 | Mosbaugh et al. |
| 2011/0212217 A1 | 9/2011 | Herranen et al. |
| 2011/0212218 A1* | 9/2011 | Herranen ............. A23K 1/1646 426/2 |
| 2012/0070516 A1 | 3/2012 | Tranquil et al. |
| 2015/0164966 A1 | 6/2015 | Vuorenmaa et al. |
| 2015/0238454 A1 | 8/2015 | Vuorenmaa et al. |
| 2016/0081368 A1 | 3/2016 | Vuorenmaa et al. |
| 2016/0081952 A1 | 3/2016 | Vuorenmaa et al. |
| 2016/0250171 A1 | 9/2016 | Vuorenmaa et al. |
| 2016/0250269 A1 | 9/2016 | Rintola et al. |

FOREIGN PATENT DOCUMENTS

| | | |
|---|---|---|
| DE | 101 06 078 A1 | 9/2002 |
| EP | 0 078 152 A1 | 5/1983 |
| EP | 0 146 738 A2 | 7/1985 |
| EP | 1 586 624 A1 | 10/2005 |
| EP | 2 343 061 A1 | 7/2011 |
| FI | 41337 B | 6/1969 |
| FI | 20110371 A | 4/2013 |
| FI | 20120287 A | 4/2013 |
| GB | 955316 A | 4/1965 |
| GB | 2 139 868 A | 11/1984 |
| GB | 2 271 282 A | 4/1994 |
| JP | S60-237008 A | 11/1985 |
| WO | WO 94/16690 A1 | 8/1994 |
| WO | WO 99/10148 A1 | 3/1999 |
| WO | WO 02/02106 A1 | 1/2002 |
| WO | WO 03/024681 A1 | 3/2003 |
| WO | WO 2006/040537 A1 | 4/2006 |
| WO | WO 2008/099051 A2 | 8/2008 |
| WO | WO 2008/154522 A1 | 12/2008 |
| WO | WO 2009/079680 A1 | 7/2009 |
| WO | WO 2009/106696 A1 | 9/2009 |
| WO | WO 2011/042613 A2 | 4/2011 |
| WO | WO 2011/055018 A2 | 5/2011 |
| WO | WO 2011/080399 A1 | 7/2011 |
| WO | WO 2011/099000 A2 | 8/2011 |
| WO | WO 2012/037297 A1 | 3/2012 |
| WO | WO 2013/060936 A1 | 5/2013 |
| WO | WO 2013/118099 A1 | 8/2013 |
| WO | WO 2013/171370 A1 | 11/2013 |
| WO | WO 2014/184430 A1 | 11/2014 |

OTHER PUBLICATIONS

Machmuler et al. Animal Feed Science Technology 71, 1998, 117-130.*

International Search Report for International Patent Application No. PCT/2014/050348 mailed Nov. 21, 2014.

Finnish Search Report for Finnish Patent Application No. 20135506 mailed Dec. 20, 2013.

Product Data Sheet SYLFAT® 2LTC tall oil fatty acid [online], Arizona Chemical, [last modified Jul. 20, 2009], retrieved Dec. 17, 2013, URL: http://www.arizonachemical.com/Global/PDS/EU_product_data_sheets/SYLFAT%C2%AE%202LTC.pdf.

European Search Report for European Patent Application No. 14797471.1 dated Dec. 6, 2016, 11 pgs.

European Search Report for European Patent Application No. 14797745.8 dated Dec. 5, 2016, 9 pgs.

European Search Report for European Patent Application No. 14797238.4 dated Dec. 7, 2016, 10 pgs.

Duncan, D.P., "Tall Oil Fatty Acids", Naval Stores, 346-349 (1989).

Gudmundur, B. et al., "Antibacterial, Antiviril and Antifungal Activities of Lipids" in "Lipids and Essential Oils as Antimicrobial Agents", John Wiley & Sons, 47-80 (2011)

Van Nevel, C.J. et al., "Effect of Fatty Acid Derivatives on Rumen Methane and Propionate in Vitro[1]", Applied Microbiology, 365-366 (1971).

Antila, M. et al., "The fatty acids of tall oil and their ethyl and glyceryl esters as animal fodder ingredients, the chemical and physical properties of the fatty acid fraction and esters prepared from this fraction", Journal ACTA Agricultureae Scandinavia, 12: 95-105, 1962, Abstract.

Beauchemic, K.A., et al., "Nutritional management for enteric methane abatement: a review", Australian Journal of Experimental Agriculture, 48: 21-27, 2008.

de Graaf et al., "Consumption of tall oil-derived phytosterols in a chocolate matrix significantly decreases plasma total and low-density lipoprotein-cholesterol levels", British Journal of Nutrition, 88: 479-488, 2002.

Grainger, C. et al., "Can enteric methane emissions from ruminants be lowered without lowering their production?", Animal Feed Science and Technology, 166-167: 308-320, 2011.

Norlin, L. "Tall Oil", Ullmann's Encyclopedia of Industrial Chemistry, published online: Jun. 15, 2000.

O'Quinn, P.R. et al., "Effects of modified tall oil and creatine monohydrate on growth performance, carcass characteristics, and meat quality of growing-finishing pigs", Journal of Animal Science, 78(9): 2376-2382, 2000.

O'Quinn, P.R. et al., "Effects of modified tall oil versus a commercial source of conjugated linoleic acid and increasing levels of modified tall oil on growth performance and carcass characteristics of growing-finishing pigs", Journal of Animal Science, 78(9): 2359-2368, 2000.

O'Quinn, P.R. et al., "Effects of modified tall oil versus conjugated linoleic acid on finishing pig growth performance and carcass characteristics", KSU Swine Day, 157-161, 1998.

Savluchinske-Feio, S. et al., "Antimicrobial activity of resin acid derivatives", Applied microbiology and Biotechnology, 72(3): 430-436, 2006.

Smith, E., et al., "Isopimaric Acid from Pinus nigra shows Activity against Multi-drug-resistant and EMRSA Strains for Staphylococcus aureus", Phytotherapy Research, 19(6): 538-542, 2005.

Snell, F. et al., "Comparative Value of Fatty Acids and Resin Acids of Tall Oil in Soaps", The Journal of the American Oil Chemist's Society, 27(8): 289-295, 1950.

"Carboxylic Acids, Fatty Acids from Tall Oil", Kirk-Othmer Encyclopedia of Chemical Technology, Copyright 1999-2014 by John Wiley and Sons, Inc., 4 pgs.

"Explanatory Notes to the Harmonized Commodity Description and Coding System", The Department of Duty Collection of the 25 General Administration of Customs, China Commerce and TradePress, published on Jan. 31, 2007, see p. 478: "Tall Oil, Whether or Not Refined". English translation of relevant parts.

* cited by examiner

USE OF TALL OIL FATTY ACID

This application is a National Stage Application of PCT/FI2014/050348, filed 9 May 2014, which claims benefit of Ser. No. 20135506, filed 14 May 2013 in Finland and which applications are incorporated herein by reference. To the extent appropriate, a claim of priority is made to each of the above disclosed applications.

FIELD OF THE INVENTION

The invention relates to use of a tall oil fatty acid, feed supplement and feed composition comprising said tall oil fatty acid.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Ruminant animals can utilize fiber-rich raw materials which have little or no nutritional value for monogastrics like the human. However, the feed conversion efficiency of ruminants is relatively low and their methane production represents a remarkable share of the world's greenhouse gas emissions. With the increasing demand of food there is a need to improve the feed conversion efficiency of ruminants and to lower their methane production. Generally, there is an increasing demand for ingredients for use in animal feeding that can modulate the microbial population in the animal digestive tract but which are readily available, well tolerated and environmentally friendly.

Fractional distillation of crude tall oil, obtained as a by-product of the Kraft process of wood pulp manufacture, produces distilled tall oil (DTO) which typically comprises over 10% resin acids and less than 90% fatty acids. Further refinement of distilled tall oil produces tall oil fatty acid (TOFA), which is available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

PURPOSE OF THE INVENTION

The purpose of the invention is to provide a new type of tall oil fatty acid/feed supplement for use in enhancing rumen fermentation and/or lowering rumen methane production.

The present inventors have surprisingly found that TOFA enhances rumen fermentation and/or lowers rumen methane production.

SUMMARY

Use of a tall oil fatty acid according to the present invention is characterized by what is presented in claim 1.

Use of a feed supplement according to the present invention is characterized by what is presented in claim 7.

Use of a feed composition according to the present invention is characterized by what is presented in claim 11.

DETAILED DESCRIPTION OF THE INVENTION

FIG. 1. Total number of Bacteria detected after 12 hours rumen simulation in the absence or presence of TOFA.

Figure 2:
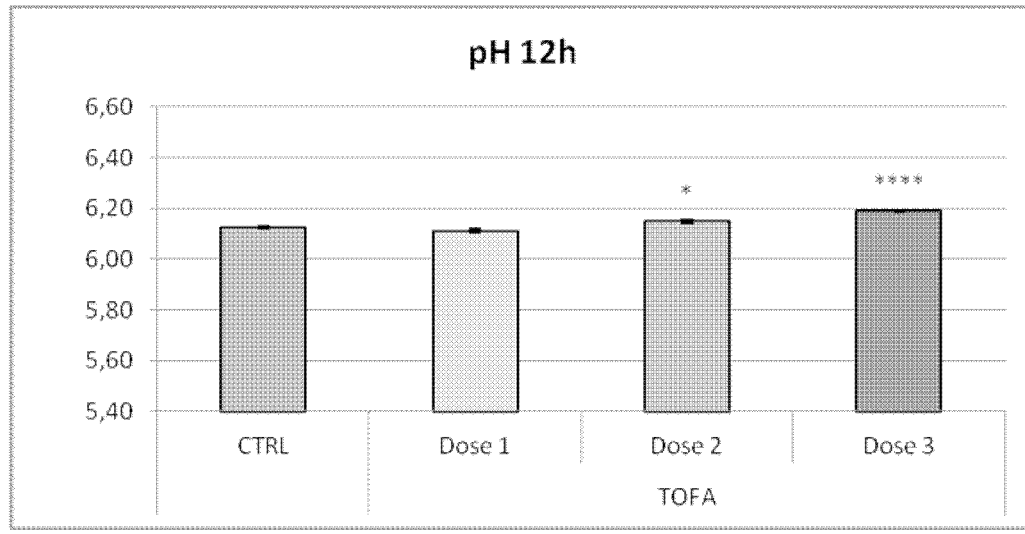

FIG. 2. pH at the end of 12 hours rumen simulation in the absence or presence of TOFA.

The present invention is based on the realization that tall oil fatty acid can be used in enhancing rumen fermentation and/or lowering rumen methane production.

In fermentation fiber, especially cellulose and hemi-cellulose, is primarily broken down into the three volatile fatty acids (VFAs), acetic acid, propanoic acid and beta-hydroxybutyric acid. Protein and non-structural carbohydrate (pectin, sugars, starches) are also fermented.

The term "tall oil fatty acid" or "TOFA" should be understood as referring to a composition obtained by distillation of crude tall oil and further refinement of distilled tall oil. TOFA typically comprises 90-98% (w/w) fatty acids. Further, TOFA may comprise 1-10% (w/w) resin acids.

In one embodiment of the present invention, the tall oil fatty acid comprises 1-10% (w/w) of resin acids.

In one embodiment of the present invention, TOFA comprises 2-9% (w/w) resin acids.

In one embodiment of the present invention, TOFA comprises 5-9% (w/w) resin acids.

In this context, the term "resin acids" should be understood as referring to a complex mixture of various acidic compounds comprised by tall oil which share the same basic skeleton including a three-fused ring. The exact composition of the resin acids present in TOFA varies e.g. according to the species of the trees the TOFA is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In one embodiment of the present invention, TOFA comprises 90-98% (w/w) of fatty acids.

The tall oil fatty acid (TOFA) is produced by refinement from distilled tall oil. Distilled tall oil (DTO) is produced by fractional distillation from crude tall oil, obtained as a by-product of the Kraft process of wood pulp manufacture.

In one embodiment of the present invention, the TOFA is dried. The TOFA can be dried by spray drying, drum drying or by any other known suitable drying method.

The present invention also relates to use of a feed supplement comprising the tall oil fatty acid in enhancing rumen fermentation and/or lowering rumen methane production.

The feed supplement is effective in enhancing rumen fermentation and/or lowering rumen methane production.

In one embodiment of the present invention, the feed supplement comprises a tall oil fatty acid which comprises 1-10% (w/w) resin acids.

In one embodiment of the present invention, the feed supplement comprises a tall oil fatty acid which comprises 2-9% (w/w) resin acids.

In one embodiment of the present invention, the feed supplement comprises a tall oil fatty acid which comprises 5-9% (w/w) resin acids.

In this context, the term "feed supplement" should be understood as referring to a composition that may be added to a feed or used as such in the feeding of animals. The feed supplement may comprise different active ingredients. The feed supplement may be added in the feed in a concentration of 0.0001-5 kg//ton of dry weight, preferably 0.005-1 kg/ton of the dry weight of the total amount of the feed. The TOFA or the feed supplement comprising the TOFA according to the invention may be added to the feed or feed supplement as such, or it may in general be further processed as desired.

Further, the TOFA or the feed supplement comprising the TOFA according to the invention may be added to the feed or feed supplement, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

In one embodiment of the present invention, the feed supplement comprises TOFA which is absorbed into a carrier material suitable for the feed composition such as sugarbeet pulp.

In one embodiment of the present invention, the feed supplement comprises TOFA which is dried.

The present invention also relates to use of a feed composition comprising the feed supplement comprising the tall oil fatty acid in enhancing rumen fermentation and/or lowering rumen methane production.

In one embodiment of the present invention, the feed composition comprises the feed supplement in an amount of 0.00001-0.5% (w/w), of the dry weight of the total amount of the feed.

In one embodiment of the present invention, the feed composition comprises the feed supplement in an amount of 0.0005-0.1% (w/w) of the dry weight of the total amount of the feed.

In one embodiment of the present invention, the method of producing a tall oil fatty acid or feed supplement further comprises a step of drying. The dying can be carried out by spray drying, drum drying or by any other known drying method.

The invention also relates to a method of enhancing rumen fermentation and/or lowering rumen methane production, comprising the step of administering to an animal the tall oil fatty acid according to the invention.

In this context, the term "harmful bacteria" should be understood as referring to any bacteria that is capable of affecting the digestive tract or health of an animal in an adverse manner, including competition for nutrients with the host animal. (In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species depending on e.g. the health of an animal and on environmental factors.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In one embodiment of the present invention, the TOFA is administered to an animal in an effective amount.

The present invention has a number of advantages. TOFA is a readily available, natural, low-cost and environmentally friendly material. Further, it is non-toxic and well tolerated. Subsequently, other benefits of the invention are e.g. lower costs per production unit and decreased environmental loads. The invention also allows the production of feed compositions and supplements at low cost.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

Methane Inhibition Test

The TOFA was manufactured by adding enough water to adjust the total dry matter (TOFA) percentage of the mixture to 18-20%, heating the mixture to +90° C., keeping the temperature at +90° C. for 120 minutes, during which time the mixture was gently stirred at 15 min intervals.

The methane inhibition test was conducted with rumen-fistulated dairy cows in order to study the potential of TOFA to decrease the rate of methane production in the rumen. Rumen fluid samples were measured for the numbers of methanogenic bacteria, as they are the methane-producing organisms. The short chain fatty acid profiles, including the concentration of branched chain fatty acids, of the samples were measured as they indicate whether TOFA had effects to ruminal fermentation.

Three rumen-fistulated, lactating dairy cows were given 6.5 g of dry TOFA /head/day for 21 days, in four portions. TOFA was first dried onto sugar beet pulp and then mixed into the compound feed. Rumen samples were taken before the dietary intervention, once a week during the TOFA feeding, and after a two-week washout period. The fifteen samples of the trial were analysed for short chain fatty acids (SCFAs) by gas chromatography and numbers of methanogens, protozoa and total bacteria by qPCR.

Results

The results show that the numbers of methane producing bacteria decreased numerically during the TOFA feeding period, while protozoa and the total number of bacteria were not affected by the product. The levels of lactic, propionic, and valeric acids and total short chain fatty acids tended to decrease in the rumen fluid during the TOFA feeding period. The TOFA tended to increase the relative proportion of butyric acid. The concentration and relative proportion of branched chain fatty acids tended to decrease as a response to dietary TOFA amendment.

Example 2

Rumen in vitro Fermentation

This experiment was conducted to study the effect of TOFA with 5% resin acids on the rumen fermentation in vitro. The treatments were prepared from a representative batch of the TOFA product. An aliquot of TOFA was heated to 90° C., mixed with finely ground sugar beet pulp (SBP), and dried to contain 375 g of dry TOFA/kg. The TOFA in the SBP carrier was tested at three doses (2 mg/g, 10 mg/g and 50 mg/g) in fermentation vessels. Control treatment contained an equal amount SBP without TOFA.

The total amount of feed in the simulation was 1 gram of dry matter per fermentation vessel. The feed contained 50% grass silage and 50% compound feed (Lypsykrossi®). Fermentation vessels were flushed with $CO_2$ passed through a hot copper catalyst for $O_2$ scavenging and sealed with thick butyl rubber stoppers. A total of 38 ml of anaerobic, reduced and temperature adjusted (+38° C.) buffer solution (see Agriculture Handbook, Vol 379 published by USDA in 1970) was introduced into each simulation vessel under the oxygen-free $CO_2$ flow. The initial pH of the fermentation medium was set to 6.8 and it was buffered with phosphate and carbonate. Each treatment was introduced in 5 replicate vessels.

Rumen fluid was taken from a rumen fistulated cow that was fed 8 kg of compound feed and about 40 kg of grass silage (about 13 kg dry matter) per day. Rumen fluid was immediately transported from the farm in a preheated thermos and was used for inoculation within 2 hours. Strained rumen fluid was added at 5% of the final volume into the serum bottles after which the vessels were sealed with butyl rubber stoppers. The simulation was continued for 12 hours at +38° C.

During the 12-hour fermentation, total gas production and pH were measured to get an idea of the general metabolic activity of the rumen microbes and the effect of the products. Additionally total microbial numbers were analysed by quantitative real time PCR.

The data was analysed using two-tailed t-test, which compares the dietary treatments against the control treatment.

Results

The gas production with the highest dose (50 mg/g) decreased the gas production significantly.

All doses of TOFA increased the total number of bacteria as compared to the control (FIG. 1).

Two of the highest TOFA doses significantly slowed down the drop of pH in the rumen fluid from the initial pH of 6.8 (FIG. 2).

The results show that TOFA is causing a shift in the rumen microbiota. It suppressed microbes with the highest gas production capacity, but stimulated the overall growth of bacteria at modest doses. The fact that pH reduction was controlled by TOFA indicates that it has an alleviating effect on rumen acidosis.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method of enhancing rumen fermentation and/or lowering rumen methane production, the method comprising:
   administering to an animal a feed and 0.00001-0.5% of a feed supplement by weight of the feed, the feed supplement comprising a tall oil fatty acid, wherein the tall oil fatty acid comprises 1-10 wt-% resin acids.

2. The method according to claim 1, wherein the tall oil fatty acid comprises 2-9% (w/w) resin acids.

3. The method according to claim 1, wherein the tall oil fatty acid comprises 5-9% (w/w) resin acids.

4. The method according to claim 1, wherein the tall oil fatty acid comprises 90-98% (w/w) fatty acids.

5. A tall oil fatty acid wherein the tall oil fatty acid is dried.

6. The method according to claim 1, wherein the tall oil fatty acid is absorbed into a carrier material.

7. The method according to claim 1, wherein the feed supplement is administered in an amount of 0.0005-0.1% (w/w) of dry weight of the feed.

8. The method of claim 1, wherein the tall oil fatty acid is dosed at 2 to 50 mg/g.

9. The method of claim 1, wherein the feed supplement consists of tall oil fatty acid.

* * * * *